United States Patent
Schurman et al.

(10) Patent No.: US 11,944,431 B2
(45) Date of Patent: **\*Apr. 2, 2024**

(54) APPARATUS AND METHOD FOR CREATING A STABLE OPTICAL INTERFACE

(71) Applicant: Masimo Corporation, Irvine, CA (US)

(72) Inventors: Matthew J. Schurman, Richboro, PA (US); Phillip William Wallace, Bernardsville, NJ (US); Walter J. Shakespeare, Macungie, PA (US); Howard P. Apple, Winter Park, FL (US); William Henry Bennett, San Jose, CA (US)

(73) Assignee: Masimo Corportation, Irvine, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 17/456,102

(22) Filed: Nov. 22, 2021

(65) Prior Publication Data

US 2022/0142517 A1    May 12, 2022

Related U.S. Application Data

(63) Continuation of application No. 16/365,022, filed on Mar. 26, 2019, now Pat. No. 11,207,007, which is a
(Continued)

(51) Int. Cl.
  *A61B 5/1455*  (2006.01)
  *A61B 5/00*  (2006.01)
  *A61B 5/145*  (2006.01)

(52) U.S. Cl.
  CPC .......... *A61B 5/1455* (2013.01); *A61B 5/0066* (2013.01); *A61B 5/14532* (2013.01);
(Continued)

(58) Field of Classification Search
  CPC . A61B 5/1455; A61B 5/14552; A61B 5/0066; A61B 5/14532; A61B 5/6832
  See application file for complete search history.

(56) References Cited

U.S. PATENT DOCUMENTS

| | | | |
|---|---|---|---|
| 4,113,354 | A | 9/1978 | Yamasita et al. |
| 4,960,128 | A | 10/1990 | Gordon et al. |

(Continued)

FOREIGN PATENT DOCUMENTS

| | | |
|---|---|---|
| WO | WO 03/105664 | 12/2003 |
| WO | WO 2006/020408 | 2/2006 |

OTHER PUBLICATIONS

Larin, K. et al., "Noninvasive Blood Glucose Monitoring with Optical Coherence Tomography," 25(12):2263-67 (2002).
(Continued)

*Primary Examiner* — Marjan Fardanesh
(74) *Attorney, Agent, or Firm* — Knobbe, Martens, Olson & Bear, LLP

(57) ABSTRACT

A system and a method for creating a stable and reproducible interface of an optical sensor system for measuring blood glucose levels in biological tissue include a dual wedge prism sensor attached to a disposable optic that comprises a focusing lens and an optical window. The disposable optic adheres to the skin to allow a patient to take multiple readings or scans at the same location. The disposable optic includes a Petzval surface placed flush against the skin to maintain the focal point of the optical beam on the surface of the skin. Additionally, the integrity of the sensor signal is maximized by varying the rotation rates of the dual wedge prisms over time in relation to the depth scan rate of the sensor. Optimally, a medium may be injected between the disposable and the skin to match the respective refractive indices and optimize the signal collection of the sensor.

11 Claims, 13 Drawing Sheets

Related U.S. Application Data continuation of application No. 15/897,917, filed on Feb. 15, 2018, now Pat. No. 10,278,626, which is a continuation of application No. 14/451,268, filed on Aug. 4, 2014, now Pat. No. 9,924,893, which is a continuation of application No. 13/544,788, filed on Jul. 9, 2012, now Pat. No. 8,831,700, which is a continuation of application No. 11/378,538, filed on Mar. 17, 2006, now Pat. No. 8,219,172.

(52) U.S. Cl.
CPC .......... *A61B 5/6832* (2013.01); *A61B 5/6833* (2013.01); *A61B 2562/146* (2013.01)

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |

(56) References Cited

U.S. PATENT DOCUMENTS

| | | |
|---|---|---|
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,583 B1 | 1/2005 | Lewandowski et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,190,994 B2 | 3/2007 | Mohler et al. |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,248,907 B2 | 7/2007 | Hogan |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,734 B2 | 12/2007 | Dogariu |
| 7,328,053 B1 | 2/2008 | Diab et al. |
| 7,332,784 B2 | 2/2008 | Mills et al. |
| 7,333,843 B2 | 2/2008 | Monfre et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |

(56) References Cited

U.S. PATENT DOCUMENTS

| | | |
|---|---|---|
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Dial |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |

(56) References Cited

U.S. PATENT DOCUMENTS

| | | |
|---|---|---|
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |

(56) References Cited

U.S. PATENT DOCUMENTS

| | | | |
|---|---|---|---|
| 9,622,693 B2 | 4/2017 | Diab | |
| D788,312 S | 5/2017 | Al-Ali et al. | |
| 9,636,055 B2 | 5/2017 | Al Ali et al. | |
| 9,636,056 B2 | 5/2017 | Al-Ali | |
| 9,649,054 B2 | 5/2017 | Lamego et al. | |
| 9,662,052 B2 | 5/2017 | Al-Ali et al. | |
| 9,668,679 B2 | 6/2017 | Schurman et al. | |
| 9,668,680 B2 | 6/2017 | Bruinsma et al. | |
| 9,668,703 B2 | 6/2017 | Al-Ali | |
| 9,675,286 B2 | 6/2017 | Diab | |
| 9,687,160 B2 | 6/2017 | Kiani | |
| 9,693,719 B2 | 7/2017 | Al-Ali et al. | |
| 9,693,737 B2 | 7/2017 | Al-Ali | |
| 9,697,928 B2 | 7/2017 | Al-Ali et al. | |
| 9,717,425 B2 | 8/2017 | Kiani et al. | |
| 9,717,458 B2 | 8/2017 | Lamego et al. | |
| 9,724,016 B1 | 8/2017 | Al-Ali et al. | |
| 9,724,024 B2 | 8/2017 | Al-Ali | |
| 9,724,025 B1 | 8/2017 | Kiani et al. | |
| 9,730,640 B2 | 8/2017 | Diab et al. | |
| 9,743,887 B2 | 8/2017 | Al-Ali et al. | |
| 9,749,232 B2 | 8/2017 | Sampath et al. | |
| 9,750,442 B2 | 9/2017 | Olsen | |
| 9,750,443 B2 | 9/2017 | Smith et al. | |
| 9,750,461 B1 | 9/2017 | Telfort | |
| 9,775,545 B2 | 10/2017 | Al-Ali et al. | |
| 9,775,546 B2 | 10/2017 | Diab et al. | |
| 9,775,570 B2 | 10/2017 | Al-Ali | |
| 9,778,079 B1 | 10/2017 | Al-Ali et al. | |
| 9,782,077 B2 | 10/2017 | Lamego et al. | |
| 9,782,110 B2 | 10/2017 | Kiani | |
| 9,787,568 B2 | 10/2017 | Lamego et al. | |
| 9,788,735 B2 | 10/2017 | Al-Ali | |
| 9,788,768 B2 | 10/2017 | Al-Ali et al. | |
| 9,795,300 B2 | 10/2017 | Al-Ali | |
| 9,795,310 B2 | 10/2017 | Al-Ali | |
| 9,795,358 B2 | 10/2017 | Telfort et al. | |
| 9,795,739 B2 | 10/2017 | Al-Ali et al. | |
| 9,801,556 B2 | 10/2017 | Kiani | |
| 9,801,588 B2 | 10/2017 | Weber et al. | |
| 9,808,188 B1 | 11/2017 | Perea et al. | |
| 9,814,418 B2 | 11/2017 | Weber et al. | |
| 9,820,691 B2 | 11/2017 | Kiani | |
| 9,833,152 B2 | 12/2017 | Kiani et al. | |
| 9,833,180 B2 | 12/2017 | Shakespeare et al. | |
| 9,839,379 B2 | 12/2017 | Al-Ali et al. | |
| 9,839,381 B1 | 12/2017 | Weber et al. | |
| 9,847,002 B2 | 12/2017 | Kiani et al. | |
| 9,847,749 B2 | 12/2017 | Kiani et al. | |
| 9,848,800 B1 | 12/2017 | Lee et al. | |
| 9,848,806 B2 | 12/2017 | Al-Ali | |
| 9,848,807 B2 | 12/2017 | Lamego | |
| 9,861,298 B2 | 1/2018 | Eckerbom et al. | |
| 9,861,304 B2 | 1/2018 | Al-Ali et al. | |
| 9,861,305 B1 | 1/2018 | Weber et al. | |
| 9,867,578 B2 | 1/2018 | Al-Ali et al. | |
| 9,872,623 B2 | 1/2018 | Al-Ali | |
| 9,876,320 B2 | 1/2018 | Coverston et al. | |
| 9,877,650 B2 | 1/2018 | Muhsin et al. | |
| 9,877,686 B2 | 1/2018 | Al-Ali et al. | |
| 9,891,079 B2 | 2/2018 | Dalvi | |
| 9,895,107 B2 | 2/2018 | Al-Ali et al. | |
| 9,913,617 B2 | 3/2018 | Al-Ali et al. | |
| 9,924,893 B2 | 3/2018 | Schurman et al. | |
| 9,924,897 B1 | 3/2018 | Abdul-Hafiz | |
| 9,936,917 B2 | 4/2018 | Poeze et al. | |
| 9,943,269 B2 | 4/2018 | Muhsin et al. | |
| 9,949,676 B2 | 4/2018 | Al-Ali | |
| 9,955,937 B2 | 5/2018 | Telfort | |
| 9,965,946 B2 | 5/2018 | Al-Ali et al. | |
| 9,980,667 B2 | 5/2018 | Kiani et al. | |
| D820,865 S | 6/2018 | Muhsin et al. | |
| 9,986,919 B2 | 6/2018 | Lamego et al. | |
| 9,986,952 B2 | 6/2018 | Dalvi et al. | |
| 9,989,560 B2 | 6/2018 | Poeze et al. | |
| 9,993,207 B2 | 6/2018 | Al-Ali et al. | |
| 10,007,758 B2 | 6/2018 | Al-Ali et al. | |
| D822,215 S | 7/2018 | Al-Ali et al. | |
| D822,216 S | 7/2018 | Barker et al. | |
| 10,010,276 B2 | 7/2018 | Al-Ali et al. | |
| 10,032,002 B2 | 7/2018 | Kiani et al. | |
| 10,039,482 B2 | 8/2018 | Al-Ali et al. | |
| 10,052,037 B2 | 8/2018 | Kinast et al. | |
| 10,058,275 B2 | 8/2018 | Al-Ali et al. | |
| 10,064,562 B2 | 9/2018 | Al-Ali | |
| 10,086,138 B1 | 10/2018 | Novak, Jr. | |
| 10,092,200 B2 | 10/2018 | Al-Ali et al. | |
| 10,092,249 B2 | 10/2018 | Kiani et al. | |
| 10,098,550 B2 | 10/2018 | Al-Ali et al. | |
| 10,098,591 B2 | 10/2018 | Al-Ali et al. | |
| 10,098,610 B2 | 10/2018 | Al-Ali et al. | |
| 10,111,591 B2 | 10/2018 | Dyell et al. | |
| D833,624 S | 11/2018 | DeJong et al. | |
| 10,123,726 B2 | 11/2018 | Al-Ali et al. | |
| 10,123,729 B2 | 11/2018 | Dyell et al. | |
| 10,130,289 B2 | 11/2018 | Al-Ali et al. | |
| 10,130,291 B2 | 11/2018 | Schurman et al. | |
| D835,282 S | 12/2018 | Barker et al. | |
| D835,283 S | 12/2018 | Barker et al. | |
| D835,284 S | 12/2018 | Barker et al. | |
| D835,285 S | 12/2018 | Barker et al. | |
| 10,149,616 B2 | 12/2018 | Al-Ali et al. | |
| 10,154,815 B2 | 12/2018 | Al-Ali et al. | |
| 10,159,412 B2 | 12/2018 | Lamego et al. | |
| 10,188,296 B2 | 1/2019 | Al-Ali et al. | |
| 10,188,331 B1 | 1/2019 | Kiani et al. | |
| 10,188,348 B2 | 1/2019 | Al-Ali et al. | |
| RE47,218 E | 2/2019 | Ai-Ali | |
| RE47,244 E | 2/2019 | Kiani et al. | |
| RE47,249 E | 2/2019 | Kiani et al. | |
| 10,194,847 B2 | 2/2019 | Al-Ali | |
| 10,194,848 B1 | 2/2019 | Kiani et al. | |
| 10,201,298 B2 | 2/2019 | Al-Ali et al. | |
| 10,205,272 B2 | 2/2019 | Kiani et al. | |
| 10,205,291 B2 | 2/2019 | Scruggs et al. | |
| 10,213,108 B2 | 2/2019 | Al-Ali | |
| 10,226,187 B2 | 3/2019 | Al-Ali et al. | |
| 10,231,657 B2 | 3/2019 | Al-Ali et al. | |
| 10,231,670 B2 | 3/2019 | Blank et al. | |
| RE47,353 E | 4/2019 | Kiani et al. | |
| 10,279,247 B2 | 5/2019 | Kiani | |
| 10,292,664 B2 | 5/2019 | Al-Ali | |
| 10,299,720 B2 | 5/2019 | Brown et al. | |
| 10,327,337 B2 | 6/2019 | Schmidt et al. | |
| 10,327,713 B2 | 6/2019 | Barker et al. | |
| 10,332,630 B2 | 6/2019 | Al-Ali | |
| 10,383,520 B2 | 8/2019 | Wojtczuk et al. | |
| 10,383,527 B2 | 8/2019 | Al-Ali | |
| 10,388,120 B2 | 8/2019 | Muhsin et al. | |
| D864,120 S | 10/2019 | Forrest et al. | |
| 10,441,181 B1 | 10/2019 | Telfort et al. | |
| 10,441,196 B2 | 10/2019 | Eckerbom et al. | |
| 10,448,844 B2 | 10/2019 | Al-Ali et al. | |
| 10,448,871 B2 | 10/2019 | Al-Ali et al. | |
| 10,456,038 B2 | 10/2019 | Lamego et al. | |
| 10,463,340 B2 | 11/2019 | Telfort et al. | |
| 10,471,159 B1 | 11/2019 | Lapotko et al. | |
| 10,505,311 B2 | 12/2019 | Al-Ali et al. | |
| 10,524,738 B2 | 1/2020 | Olsen | |
| 10,532,174 B2 | 1/2020 | Al-Ali | |
| 10,537,285 B2 | 1/2020 | Shreim et al. | |
| 10,542,903 B2 | 1/2020 | Al-Ali et al. | |
| 10,555,678 B2 | 2/2020 | Dalvi et al. | |
| 10,568,553 B2 | 2/2020 | O'Neil et al. | |
| RE47,882 E | 3/2020 | Al-Ali | |
| 10,608,817 B2 | 3/2020 | Haider et al. | |
| D880,477 S | 4/2020 | Forrest et al. | |
| 10,617,302 B2 | 4/2020 | Al-Ali et al. | |
| 10,617,335 B2 | 4/2020 | Al-Ali et al. | |
| 10,637,181 B2 | 4/2020 | Al-Ali et al. | |
| D886,849 S | 6/2020 | Muhsin et al. | |
| D887,548 S | 6/2020 | Abdul-Hafiz et al. | |
| D887,549 S | 6/2020 | Abdul-Hafiz et al. | |
| 10,667,764 B2 | 6/2020 | Ahmed et al. | |

(56) References Cited

U.S. PATENT DOCUMENTS

| | | |
|---|---|---|
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 11,207,007 B2 | 12/2021 | Schurman et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0267105 A1 | 12/2004 | Monfre et al. |
| 2005/0020892 A1 | 1/2005 | Acosta et al. |
| 2005/0055276 A1 | 3/2005 | Kiani et al. |
| 2005/0090725 A1 | 4/2005 | Page et al. |
| 2005/0190372 A1 | 9/2005 | Dogariu |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189860 A1 | 8/2006 | Hacker et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |

(56) References Cited

U.S. PATENT DOCUMENTS

| | | |
|---|---|---|
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Ai-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |

(56) References Cited

U.S. PATENT DOCUMENTS

| | | |
|---|---|---|
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0117070 A1 | 4/2019 | Muhsin et al. |
| 2019/0216370 A1 | 7/2019 | Schurman et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |

OTHER PUBLICATIONS

Partial Search Report with Invitation to Pay Fees, from PCT/2007/006666, dated Apr. 24, 2008.

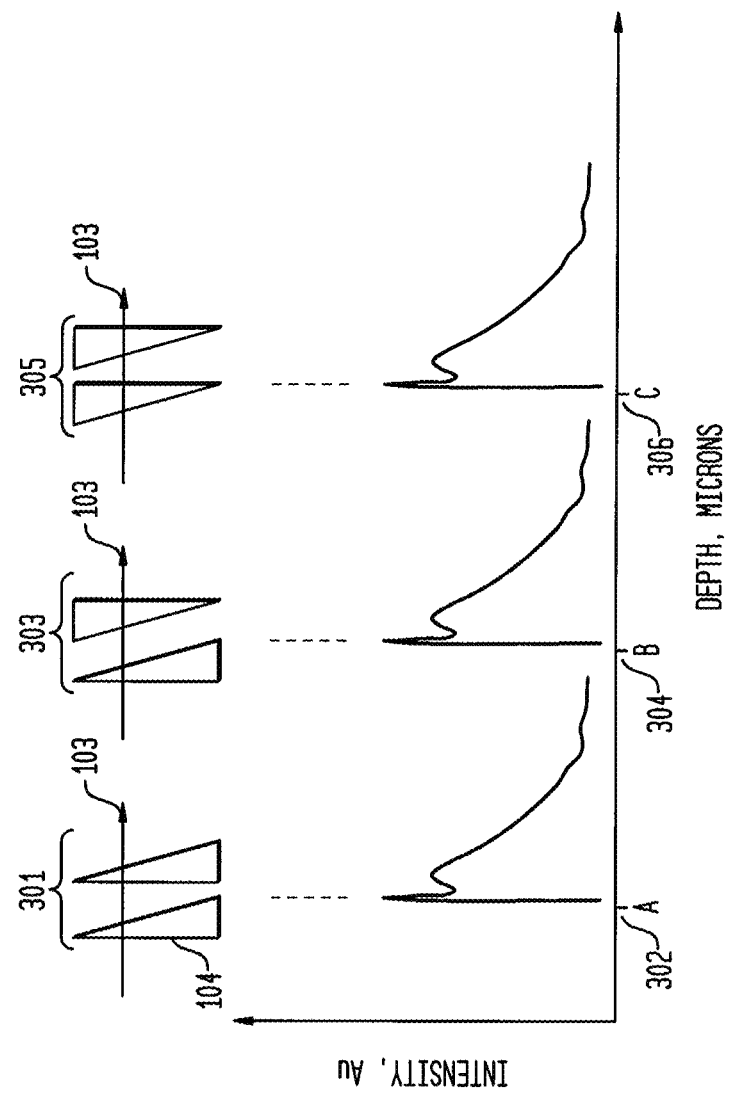

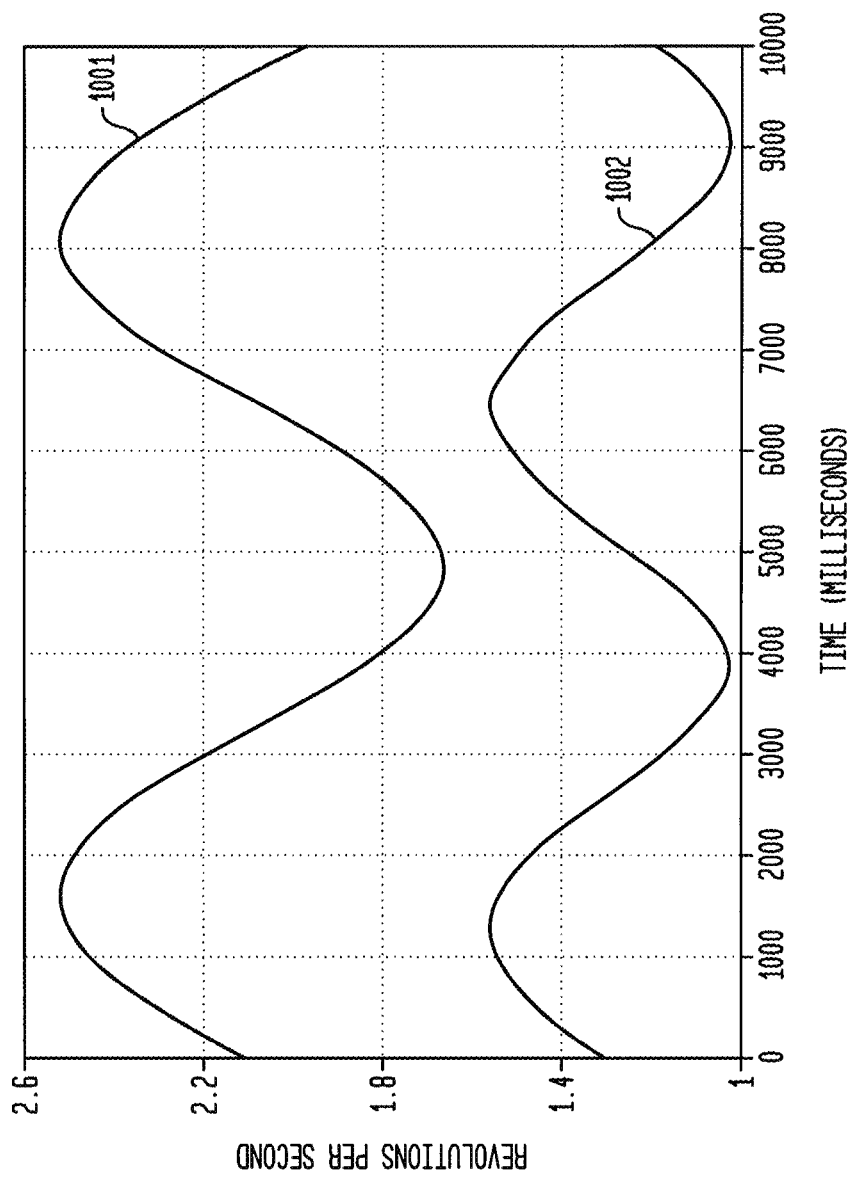

APPARATUS AND METHOD FOR CREATING A STABLE OPTICAL INTERFACE

CROSS-REFERENCE TO RELATED APPLICATIONS

This application is a continuation of U.S. application Ser. No. 16/365,022, filed Mar. 26, 2019, titled "Apparatus and Method for Creating a Stable Optical Interface," which is a continuation of U.S. application Ser. No. 15/897,917, filed Feb. 15, 2018, now U.S. Pat. No. 10,278,626, titled "Apparatus and Method for Creating a Stable Optical Interface," which is a continuation of U.S. application Ser. No. 14/451,268, filed Aug. 4, 2014, now U.S. Pat. No. 9,924,893, titled "Apparatus and Method for Creating a Stable Optical Interface," which is a continuation of U.S. application Ser. No. 13/544,788, filed Jul. 9, 2012, now U.S. Pat. No. 8,831,700, titled "Apparatus and Method for Creating a Stable Optical Interface," which is a continuation of U.S. application Ser. No. 11/378,538, filed Mar. 17, 2006, now U.S. Pat. No. 8,219,172, titled "System and Method for Creating a Stable Optical Interface." All of the above-identified applications are hereby incorporated by reference herein in their entireties and made a part of this specification.

BACKGROUND

Field of the Invention

The present invention relates generally to stabilizing an optical interface and, more specifically, to creating a reproducible and stable optical interface between biological tissue and an optical blood glucose sensor.

Description of the Related Art

Monitoring of blood glucose concentration levels has long been critical to the treatment of diabetes in humans. Current blood glucose monitors involve a chemical reaction between blood serum and a test strip, requiring an invasive extraction of blood via a lancet or pinprick. Small handheld monitors have been developed to enable a patient to perform this procedure anywhere, at any time. But the inconvenience of this procedure—specifically the blood extraction and the use and disposition of test strips—has led to a low level of compliance. Such low compliance can lead to serious medical complications. Thus, a non-invasive method for monitoring blood glucose is needed.

Studies have shown that optical methods can detect small changes in biological tissue scattering related to changes in levels of blood sugar. Although highly complex, a first order approximation of monochromatic light scattered by biological tissue can be described by the following simplified Equation 1:

$$I_R = I_0 \exp[-(\mu_a + \mu_s)L] \qquad \text{Eq. 1}$$

where $I_R$ is the intensity of light reflected from the skin, $I_O$ is the intensity of the light illuminating the skin, $\mu_a$ is the absorption coefficient of the skin at the specific wavelength of light, $\mu_s$ is the scatter coefficient of the skin at the specific wavelength of light, and L is the total path traversed by the light. From this relationship, it can be seen that the intensity of the light decays exponentially as either the absorption or the scattering of the tissue increases.

It is well established that there is a difference in the index of refraction between blood serum/interstitial fluid (blood/IF) and membranes of cells such as blood cells and skin cells. (See, R. C. Weast, ed., CRC Handbook of Chemistry and Physics, 70th ed., (CRC Cleveland, Ohio 1989)). This difference can produce characteristic scattering of transmitted light. Glucose, in its varying forms, is a major constituent of blood/IF. The variation of glucose levels in blood/IF changes its refractive index and thus, the characteristic scattering from blood-perfused tissue. In the near infrared wavelength range (NIR), blood glucose changes the scattering coefficient more than it changes the absorption coefficient. Thus, the optical scattering of the blood/IF and cell mixture varies as the blood glucose level changes. Accordingly, an optical method presents a potential option for non-invasive measurement of blood glucose concentration.

Non-invasive optical techniques being explored for blood glucose application include polarimetry, Raman spectroscopy, near-infrared absorption, scattering spectroscopy, photoacoustics and optoacoustics. Despite significant efforts, these techniques have shortcomings such as low sensitivity, low accuracy (less than current invasive home monitors) and insufficient specificity of glucose concentration measurement within the relevant physiological range (4-30 mM or 72-540 mg/dL). Accordingly, there is a need for an improved method to non-invasively monitor glucose.

Optical coherence tomography, or OCT, is an optical imaging technique using light waves that produces high resolution imagery of biological tissue. OCT creates its images by focusing a beam of light into a medium and interferometrically scanning the depth of a linear succession of spots and measuring the absorption and/or the scattering of the light at different depths in each successive spot. The data is then processed to present an image of the linear cross section of the medium scanned. It has been proposed that OCT might be useful in measuring blood glucose.

One drawback associated with using OCT for monitoring blood glucose is the signal noise associated with optical interferometry, also known as speckle. As discussed in U.S. application Ser. No. 10/916,236 by M. Schurman, et al., entitled "Method and Apparatus for Monitoring Glucose Levels In A Biological Tissue," to reduce speckle, a glucose monitor incorporating OCT methodology may scan a beam of collimated light continuously and laterally across a two-dimensional surface area of a patient's tissue or skin, while interferometrically scanning the tissue in depth. Preferably, the scanning is accomplished with a small, lightweight, and robust mechanism that can be incorporated into a sensor to be used in a fiber-optics based product or, alternately, a non fiber-optics based product. One main objective of using this type of sensor is to generate a reproducible stable optical interface between the subject's skin and optical path of the sensor in order to take multiple readings from the same lateral location on the skin while maintaining the integrity of the optical interface. As discussed below, there are multiple problems associated with providing and maintaining a stable and reproducible optical interface between an OCT sensor and the skin of a patient.

Two Basic Optic Designs

Two well known sensor designs that use OCT are schematically shown in FIGS. 1 and 2. FIG. 1 shows a design based on the use of two rotating wedge prisms to change the angle of collimated light incident on a focusing lens. In FIG. 1, incoming light beam 101 hits a collimating lens 102, which splits the beam 101 into multiple parallel beams of light, or collimated light 103. The collimated light 103 then passes through one or more wedge prisms 104, which are rotating at predefined rates. As shown in FIG. 1, dual rotating wedge prisms 104 generate an angular deviation in the collimated light 103 from the optical axis of the sensor, which is the "centerline" axis passing through the elements of the sensor, perpendicular to the surface area of skin 109 to be tested. By deviating the angle of the collimated light 103, the focal point of the light moves around on a focal plane of an optical window 108 that is flush against the skin 109, thereby scanning different lateral locations on the skin 109. As shown at 105, once passing through wedge prisms 104, the parallel rays of collimated light 103 may be angled away from the optical axis, depending on what portion of the wedge prisms 104 the collimated light 103 passes through. The angled beams 105 then pass through a focusing lens 106, and begin to focus together to a focal point 107 at the bottom surface of an optical window 108.

FIG. 2 shows a similar concept to FIG. 1, however the dual wedge prisms 104 of FIG. 1 are replaced with an angled mirror 201, for example, a 45 degree angled mirror, that oscillates along two axes, thereby deviating the angle of collimated light 103 from the optical axis in order to move the focal point 108 around on the surface area of skin 109. Accordingly, this OCT sensor design is well known in the art. Both designs facilitate scanning an area of skin by deviating the angle of collimated beam 103 from the optical axis, thereby moving the focal point 107 a proportional distance laterally in the focal plane along the bottom of the optical lens 108, and, accordingly, along the surface area of the patient's skin 109.

While both sensor designs provide mechanisms for incorporating OCT into a noninvasive blood glucose sensor, there are several drawbacks associated with the above designs as described below.

Variations in Optical Path Length

One drawback associated with the dual wedge prism sensor design of FIG. 1 is illustrated in FIG. 3. In an interferometer, the optical path length of a beam of light is determined by the physical or geometric path length of the beam and the index of refraction of the medium which the beam is passing through as shown in Equation 2:

$$L_{OPT} = n \cdot L_{GEO} \qquad \text{Eq. 2}$$

where "$L_{OPT}$" is the optical path length, "n" is the index of refraction, and "$L_{GEO}$" is the geometric or physical path length.

As shown in FIG. 3, depending on the position of the wedge prisms 104 at the time the collimated beam 103 shines through, while the geometric path length of the collimated beam 103 stays the same, the index of refraction changes due to the changing thickness of the wedge prisms 104 as the prisms rotate, thereby altering the optical path length of the collimated beam 103. This continuous change in the thickness of the wedge prisms 104 continuously alters the optical path length of the collimated beam 103 as it passes through. As shown in FIG. 3, the placement of the wedges may extend the length of the optical path, making it seem as though the skin 109 is moving away from the sensor. Thus, three optical scans taken through the dual wedge prisms 104 when the prisms 104 are in different rotated positions produce three scans beginning at different positions in depth. Since the sensor data is an average of multiple scans, if each scan begins at a different position in depth, the resulting ensemble average will not be representative of a true averaging of multiple scans.

For example, in FIG. 3, when the collimated beam 103 passes through the thinnest area of the wedge prisms 104, as shown at 301, the sensor begins to collect data at Depth A, interpreting the interface between the optical window 108 and the skin 109 to be at Depth A, as shown at 302. However, when the collimated beam 103 passes though a thin portion of the first wedge prism and a thick portion of the second wedge prism, as shown at 302, the sensor begins to collect data at Depth B, interpreting the interface between the optical window 108 and the skin 109 to be at Depth B, as shown at 304. Further, when the collimated beam 103 passes through the thickest portion of both wedge prisms, as shown at 305, the sensor begins to collect data at Depth C, interpreting the interface between the optical window 108 and the skin 109 to be at Depth C, as shown at 306. Since typically multiple scans (e.g., greater than 100 scans) are taken and then averaged to reduce speckle, scans taken at different positions in depth cannot be averaged. Thus, a solution to this problem is desired.

Another drawback associated with the dual wedge prism sensor is the distortion of the scan along the depth axis or z-axis of the light beam entering and exiting the skin. If the rotation speed of the wedge prisms 104 is several orders of magnitude larger than the depth scan rate of the optical sensor, then the depth scale measured by the scan is either "stretched" or "shrunk" by the entire amount of the difference in optical path induced by the changing thickness of the wedge prisms 104. However, if the rotation speed of the wedge prisms 104 is much slower than the depth scan rate, then the changing thickness of the wedge prisms 104 has a minimal effect on the depth scale. For example, if the depth scans occur at 60 Hz, which means that the sensor completes one depth scan within in $\frac{1}{60}^{th}$ of a second, and the prisms rotate at 3600 rpm, then each wedge prism makes a full rotation during the time it takes the sensor to complete one depth scan. Because the thickness of each wedge prisms varies as the prisms rotate, the optical path length changes during each depth scan, which distorts the depth data collected by the sensor by changing the depth scale during a single scan. Thus, there is an optimization that must occur between the depth scan rate and the prism rotation rate such that the entire surface area is thoroughly scanned while minimizing the z-axis scan distortion.

Scan Pattern Stability

Accordingly, it is desired is that each depth scan be taken at a different lateral position on the surface of the skin 109 such that the ensemble of all the depth scan positions are randomly and uniformly distributed throughout the scan region. The lateral locations of each depth scan must be spatially independent to 1) effectively encompass regions of blood glucose change during a sensor reading and 2) effectively reduce speckle. However, a problem associated with the dual wedge prism sensor in FIG. 1 and the oscillating mirror sensor in FIG. 2 is the inability to capture each depth scan position due to the angular velocity of the wedge prism(s) 104 or the oscillation rate of the angled mirror 201 being harmonic in phase with the depth scan rate of the optical sensor, i.e., the frequency of the angular velocity is a multiple or integral of the depth scan rate of the sensor. When either the angular velocity or oscillation rate is an integral of the depth scan rate, the two rates "beat" against each other, and produce a loss of conformal coverage of the surface area of the skin 109 being scanned.

As shown in FIG. 4B, when using a single rotating wedge prism or oscillating angled mirror in a sensor as described above, the optimal result of multiple depth scans is a circle pattern on the surface area of the skin 109, which each "dot" representing a depth scan. Each depth scan occurs along the path of this circle pattern, effectively breaking the circle up into a series of scanned points. However, if the angular velocity is an integral or harmonic of the depth scan rate, the depths scans begin to overlap in location, thereby producing an incomplete circle pattern and a loss of spatially independent depth scans, as shown in FIG. 4A. With an overlap of depth scans, the same locations of tissue are scanned, causing less speckle reduction and poor imaging of structures within the scanned tissue. The problem becomes even more pronounced in the case of a sensor with two wedge prisms, as shown in FIG. 4C.

Focal Plane Instability

Another challenge presented by both the wedge prism design in FIG. 1 and the oscillating mirror design in FIG. 2 is the inability to maintain the focal point 107 of the focused collimated beam on the focal plane, or the interface between the optical window 108 and the surface area of the skin 109 being scanned. Optical lenses do not project an image onto a flat plane, such as the flat bottom surface of the optical window 108, but, instead, naturally project an image onto a curved surface, much like the curved interior of the eye. This curved surface is well known as a Petzval surface. Thus, as the collimated light 103 enters the focusing lens 106, the focal point 107 of the collimated light 103 traces out a curved focal plane or Petzval surface based on the design of the focusing lens 106, caused by the angular deviation from the optical axis due to the wedge prisms 104 in FIG. 1 or the angled mirror 201 in FIG. 2. Thus, the flat bottom of the optical window 108 does not allow the focal point 107 to remain on the focal plane.

When the focal point 107 moves off of the Petzval surface, the efficiency of the focused light being collected begins to drop, since focal plane is where the light capture is maximized. Additionally, the depth scale of the focused light is affected such that the displacement of the focal point 107 off of the focal plane results in an equivalent loss in the depth scale of the signal. This results in a blurring of the optical axis, causing measurable details within the skin to be blurred or washed out. Thus, a displacement of the focal point off the focal plane results in a reduction in the sensor signal intensity and a blurring of the optical axis.

Additionally, optical lenses are not perfect. Therefore, as the focal point 107 moves away from the optical axis due to the rotating wedge prisms 104 or the oscillating angled mirror 201, the focused beam drifts away from the skin 109 and back towards the focusing lens 106, and, thus, moves off the focal plane. As discussed above, when the focal point 107 is no longer on the focal plane, the collection efficiency of the light drops, resulting in the collected data incorrectly indicating a reduction in power. This, in turn, alters the depth of the focused beam, thereby unwittingly washing out details in the skin and lowering the resolution and integrity of the scan.

Skin/Sensor Optical Interface

The surface of the skin is "rough" relative to the light entering and exiting the skin during an optical scan. This is well known as optical roughness. Additionally, the refractive index of the skin being scanned typically is different from the refractive index of the material of an optical window of a sensor. As shown in FIG. 5A, the optical window 503 is not necessarily flush against the surface of the skin 504, due to optical roughness 505 of the skin. Accordingly, as incident light 501 is directed towards the skin, some of the light is reflected and/or diffracted, as shown at 502, because there is a mismatch between the index of refraction of the optical window 503 and the index of refraction of the skin 504. This mismatch of refractive indices and, in addition, the space between the skin 504 and the optical window 503 due to the optical roughness 505 reduces the reliability of data taken by the sensor.

FIG. 5B displays two scans taken at the same location on the skin but measured at different points in time with constant optical contact between the skin 109 and the optical window 108 of a sensor. Such scans may be produced by either the dual wedge prism sensor of FIG. 1 or the angled mirror sensor of FIG. 2. Data line 506 represents an averaged optical scan taken at Time 0 while data line 507 represents an averaged optical scan taken thirty minutes after Time 0. Typically, the focused beam hits the interface between the optical window 503 and the skin 504, a sharp rise or peak in the signal is produced, as shown at peaks 510 and 511. The signal then drops as the beam moves through the skin 504 and begins to rise again as the beam hits the interface between the epidermis and dermis layers, as shown at peaks 508 and 509. The signal again drops and continues to drop as the beam reaches the desired depth then returns back to the sensor.

As shown in FIG. 5B, while constant optical contact is maintained between the skin 504 and the optical window 503 of the sensor, over time the optical signal drifts, as illustrated by the peaks at the interface between the dermis and epidermis layers, which rises over time, from peak 508 at Time 0 to peak 509 at Time 0+30 minutes. However, the peak at the interface between the optical window 503 and the skin 504 drops over time, from peak 510 at Time 0 to peak 511 at Time 0+30 minutes. This change in signal intensity is due to a gradual change in the optical interface created by an accumulation of sweat and skin oils at the interface of the optical window 503 and the skin 504, as shown at 512 in FIG. 5C, which serves as an optical transition for the incident light 501 to efficiently travel from the optical window 503 to the skin 504. Additionally, the accumulation of sweat and skin oils smoothes out the optical roughness of the skin. Although the refractive index between the optical window 503 and the skin 504 will stabilize or reach an equilibrium value due to sweat, oil, and other fluids produced by the skin over time, this process could take upwards of 60-90 minutes. Unfortunately, these changes in signal intensity over this extended period of time may completely mask the changes that are occurring along the OCT signal, and thus prevent proper correlation of changes in the OCT signal to changing glucose levels, as discussed in U.S. Provisional Applications Nos. 60/671,007 and 60/671,285, both entitled "Method For Data Reduction and Calibration of an OCT-Based Blood Glucose Monitor." Thus, multiple scans taken over time cannot produce a reliable measurement from the same lateral location on the skin. In addition, a patient would be required to place the sensor onto his or her skin and wait 60-90 minutes before using it, in order to receive reliable and reproducible results, which creates an inefficient sensor.

Thus, a need exists for an optical sensor for measuring blood glucose levels and other physiological effects that overcomes the deficiencies discussed above.

SUMMARY OF THE DISCLOSURE

According to one embodiment of the present invention, a system for generating a stable and reproducible optical interface includes an OCT-based interferometer connected to an optical sensor that utilizes a collimated beam of light and comprises dual wedge prisms to move the collimated beam to different lateral locations on the skin, and a disposable optical lens apparatus that attaches to the skin surface using an adhesive, where the disposable optical lens apparatus comprises a focusing lens and an optical window that interfaces directly with the skin. Alternately, the optical sensor may utilize an angled mirror that oscillates along two axes to move the beam of light to different lateral locations on the skin surface.

By using a disposable optical lens apparatus, a patient may place the sensor onto the optical lens apparatus, take a reading, then remove the sensor and leave the optical lens apparatus attached to his or her skin, for example, on an arm. When another reading is taken at a later time, the patient simply reattaches the sensor to the optical lens apparatus, guaranteeing that the lateral location of the sensor remains the same, in order to produce a comparable optical scan. At some point in time, the patient may remove the disposable optical lens apparatus and discard it, only to replace it with another. Thus, the disposable optical lens apparatus may be made from different materials, such as, for example, glass, plastic, or other polymer material, and may be customized for each patient's needs. A computer also may be connected to the optical sensor and/or interferometer, where the computer manipulates the sensor data and produces physiological data, such as blood glucose levels.

As mentioned above, multiple scans may be taken during a single sensor use and then averaged together to reduce or remove the speckle associated with an OCT-based system. To account for variations in the optical path length of the collimated beam produced by the varying thicknesses of the rotating dual wedge prisms, the resulting scan data is manipulated. According to an embodiment of the present invention, a method for resolving the variations in optical path length includes the steps of (i) locating the first peak, which represents the interface between the optical window and the patient's skin, of the first scan taken by the sensor, (ii) locating the first peak in each subsequent scan taken during the single use, and (iii) normalize each first peak in the subsequent scans against the peak of the first scan. The method further comprises the step of (iv) averaging the normalized scans to produce an averaged scan result. To locate the peaks, algorithms such as Gaussian peak fitting and second-derivative residual methods may be used and are well known within the field of the invention.

An alternate embodiment of the present invention presents a more time-efficient method for resolving the variations in the optical path length. The method includes the steps of (i) setting a peak threshold trigger in the signal intensity and (ii) holding off of true data acquisition until the signal hits the threshold trigger. Once signal reaches the threshold trigger, the system begins to collect the scan data. Different optical arrangements may require different threshold triggers, where optical arrangements may vary due to the angle of the wedge prisms in the optical sensor. However, to optimize the threshold trigger, at least a 10 db difference may exist between the threshold trigger and the first peak intensity value, where the signal intensity is measured in decibels. For example, if the first peak measures 60 db, then the threshold trigger is set to less than or equal to 50 db. Additionally, the threshold trigger may be set above the highest noise peak produced by the signal until the focused beam hits the optical window, where the signal begins to rise in intensity. For example, if the highest noise peak is 30 db and the first intensity peak reaches 60 db, then setting a threshold trigger between 30 db and 50 db is preferable. Since the most useful data is acquired beginning typically around 150 microns in depth (within the dermis layer of the skin), and the first peak in intensity typically occurs around 20 or 30 microns in depth, by setting a threshold trigger near the rise of the first signal peak, any mismatch in the optical path length will be less than half the coherence length of the optical sensor system, which is below the resolution of the interferometer.

The coherence length of the optical sensor system, which is a measure of the depth resolution of the system, is broadly inversely related to the bandwidth of the optical source of the system, such as, for example, a superluminescent diode. Thus, as the bandwidth of the optical source increases, the coherence length of the system decreases, and accordingly, the depth resolution of the system improves. The interface between the optical sensor and the skin has a specific peak intensity value, for example, 60 dB, and the width of the peak is the coherence length of the optical sensor system, for example, 30 microns. However, for each depth scan, the optical sensor/skin interface peak doesn't always occur at the exact location in depth, i.e., the peak location may be offset by a few microns in depth. If, for example, the threshold trigger is set to a value that is near the signal peak intensity value, then the offset of the location of each peak value for each depth scan cannot be more than a fraction of the coherence length, which is below the resolution of the optical system. Thus, the offset does not affect the data collected by the sensor and the depth scans may be averaged to reduce speckle and to produce an accurate sensor reading.

According to an aspect of the embodiment, the optical sensor system may be set to acquire data once the focused beam reaches a specific structural feature. For example, the threshold trigger may be set to correspond to an intensity value of light once the focused light reaches the interface between the skin and the optical window, which may occur, for example, at a depth of one-half of a millimeter ("mm"). Thus, if the optical window/skin interface occurs at an intensity value of 60 dB, then the trigger threshold may be set to a value of 50 dB. Therefore, the optical window/skin interface becomes a reference point for each depth scan to be lined up against, in order for the depth scans to be averaged.

According to another embodiment of the present invention, a method for minimizing the distortion in the depth scale due to change in thickness of the dual wedge prisms as they rotate includes the step of optimizing the depth scan rate versus the prism angular velocity in order to minimize any distortion of the scan in depth, or along the z-axis. If the depth scans occur at a rate at or near the angular velocity of the wedge prism, then each depth scan performed by the sensor occurs within a time period close to the time period of a single rotation of the wedge prisms. As discussed above, because the wedge prisms are not a uniform thickness and the thickness affects the refractive index and the optical path length, as the prisms rotate, the depth of each depth scan is distorted within a single scan because the optical path length is changing during a single scan when the time periods are close or exact. To prevent this problem, the method includes the step of setting the angular velocity of the wedge prisms to a value such that the lateral position of the scan spot on the skin surface moves a distance that is less than ten times ("10×") a diameter of the scan spot during the data acquisition of a single depth scan. This method allows the optical path length to remain stable during each depth scan taken.

In yet another embodiment of the present invention, a method for stabilizing the scan pattern of the optical sensor includes the step of (i) setting the angular velocity of the wedge prisms to a non-harmonic phase value in relation to the depth scan rate. By doing so, conformal coverage of the scanning area may be achieved. However, due to the drift of the angular velocities common in such a system, it is likely that the angular velocity will drift into a harmonic phase of the depth scan rate, and conformal coverage will be lost.

Thus, the method further comprises the steps of (ii) varying the angular velocities of the dual wedge prisms during the total time of an entire sensor reading (i.e., 1500 scans), and (iii) varying the angular velocities of each wedge prism with respect to the other wedge prism over the total time of the sensor reading. By varying both the angular velocity of the wedge prisms over time in relation to the depth scan rate, and the angular velocity of each wedge prism over time in relation to the other wedge prism, conformal coverage of the scan surface area is maximized. According to an aspect of the present embodiment, the method may be modified to vary the oscillation rate of the angled mirror in the mirror sensor such that the oscillation rate in both axes of movement is not a harmonic of the depth scan rate of the sensor.

According to an alternate embodiment of the present invention, in an optical sensor with rotating dual wedge prisms, two harmonically related phase signals may be used to vary the angular velocities of each wedge prism so long as the time period of one phase signal associated with one of the wedge prisms is several times longer than the time period of one phase signal associated with the other wedge prism, and both phase signals are non-harmonic values of the depth scan rate. For example, if 2.0 Hz and 0.02 Hz are the angular velocities maintained over time of the wedge prisms, and the depth scan rate is 57 Hz, the problem is minimized and conformal coverage of the scan pattern is maximized. The embodiment encompasses numerous ways to vary the angular velocity of the wedge prisms, for example, a saw tooth wave, a sinusoidal wave, a triangle wave, etc.

In yet another embodiment of the present invention, a method for optimizing an amount of light entering and exiting an area of skin includes modifying the disposable optical lens as described above by incorporating a dome shape to the bottom surface of the optical window. The dome shape is designed to represent the Petzval surface of the focusing lens, and follows the variation in the focal point displacement that occurs as the focal point deviates from the optical axis through increasing incidence angles of the focused beam. Thus, the Petzval surface rests between the skin and the optical window of the disposable. Additionally, the Petzval surface also improves the interface between the disposable apparatus and the skin by stabilizing the local pressure on the skin in the vicinity of the depth scans. For a flat optical window, the pressure on the skin is distributed widely across the entire skin interface of the optical window, which is a relatively wide area. This wide distribution of pressure reduces the optical coupling efficiency of the sensor. Accordingly, the dome shape of the Petzval surface concentrates the pressure on the skin tissue towards the center of the dome where the scan is taking place, which optimizes the optical coupling efficiency of the sensor.

According to another aspect of the present embodiment, a pedestal shape may be incorporated onto the skin interface side of the optical window, to stabilize the local pressure on the skin in the vicinity of the depth scans by distributing the pressure along the plateau edge of the pedestal, thereby improving the optical contact.

The Petzval surface facilitates maintaining the focal point on the surface skin and reducing the blurring of the optical axis and maximizing the uniformity of light captured entering and exiting the skin at all points in the area scan. Using the Petzval surface, whenever the focused beam hits the surface of the skin, it is focused and maximized, providing the highest efficiency of the light as well as maintaining the same distance in depth that would be available along the optical axis due to the skin wrapping around the Petzval surface. The size of the Petzval surface is a function of the focusing lens design in the disposable apparatus. Both depth resolution and optical collection efficiency are optimized by maintaining the focal point on the Petzval surface.

According to another embodiment of the present invention, a method for improving the optical interface between a sensor and a surface of the skin includes the step of using an index matching medium at this optical interface, where the medium improves and stabilizes the optical interface and provides an optical transition for an optimal amount of incident light from the sensor to pass through to the skin. A wide variety of mediums that can be used, each with differing optical properties and viscosities, such as, for example, fluids such as glycerin, saline, and mineral oil, gels, such as medical gels or a gel moleskin, or adhesive-type materials, so long as the refractive index of the medium is less than the refractive index of the disposable apparatus. Preferably, the index matching medium provides a thin conformal coating on the skin and the associated disposable interface, and smoothes the optical roughness of the skin, reducing the loss of incident light entering the skin. By using an index matching medium, a patient need not wait the 60-90 minutes for the interface of the disposable and the skin to stabilize, but may use the OCT sensor at any given time by simply connecting it to the disposable optical lens apparatus adhered to the skin.

Additionally, the index matching medium smoothes out the relatively rough surface of the skin, which may cause a scattering of the focused beam at the skin surface. Accordingly, the index matching medium coats the skin and reduces the optical roughness of the skin surface, thereby optimizing the intensity of the light that goes into and comes out of the skin.

BRIEF DESCRIPTION OF THE DRAWINGS

The present invention will be more readily understood from the detailed description of the preferred embodiment(s) presented below considered in conjunction with the attached drawings, of which:

FIG. 3 graphically shows how the relative position of an object being scanned by a rotating wedge prism optical scanning apparatus changes due to the orientation of the wedge prism;

FIG. 10A is a graphical illustration of varying the angular velocities of dual wedge prisms in an optical scanning apparatus over time.

DETAILED DESCRIPTION OF SPECIFIC EMBODIMENTS

Figure 1:
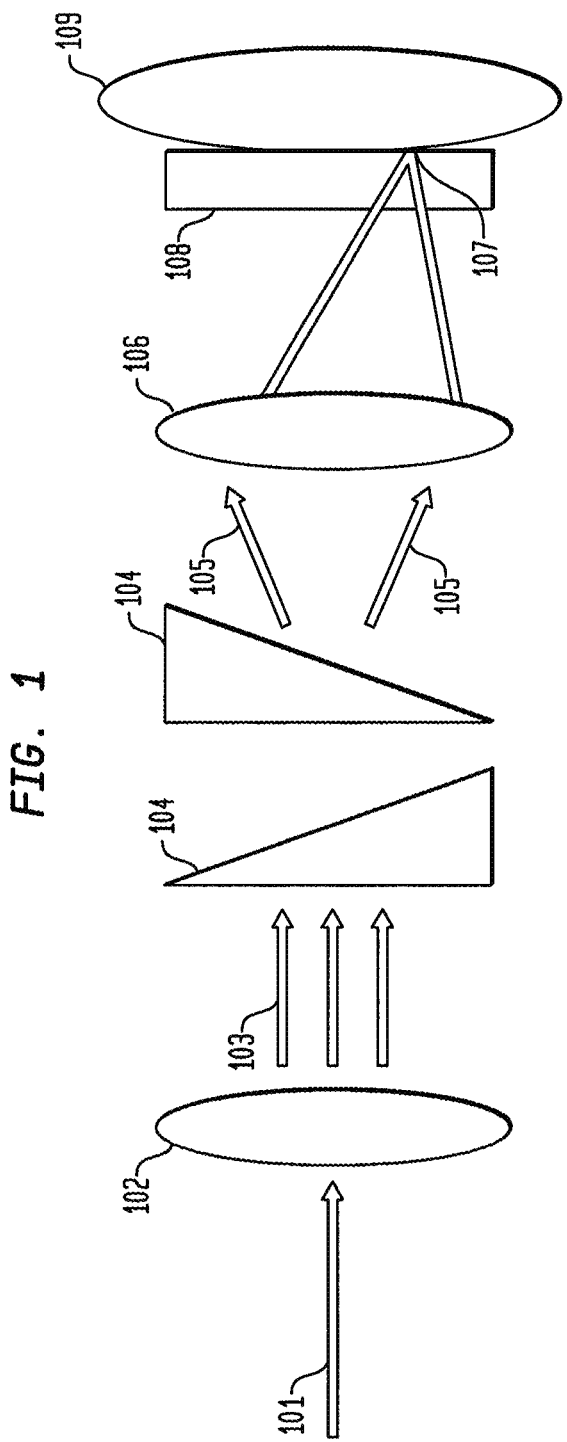
FIG. 1 illustrates a rotating dual wedge prism optical scanning apparatus, according to an embodiment of the present invention.
Figure 2:
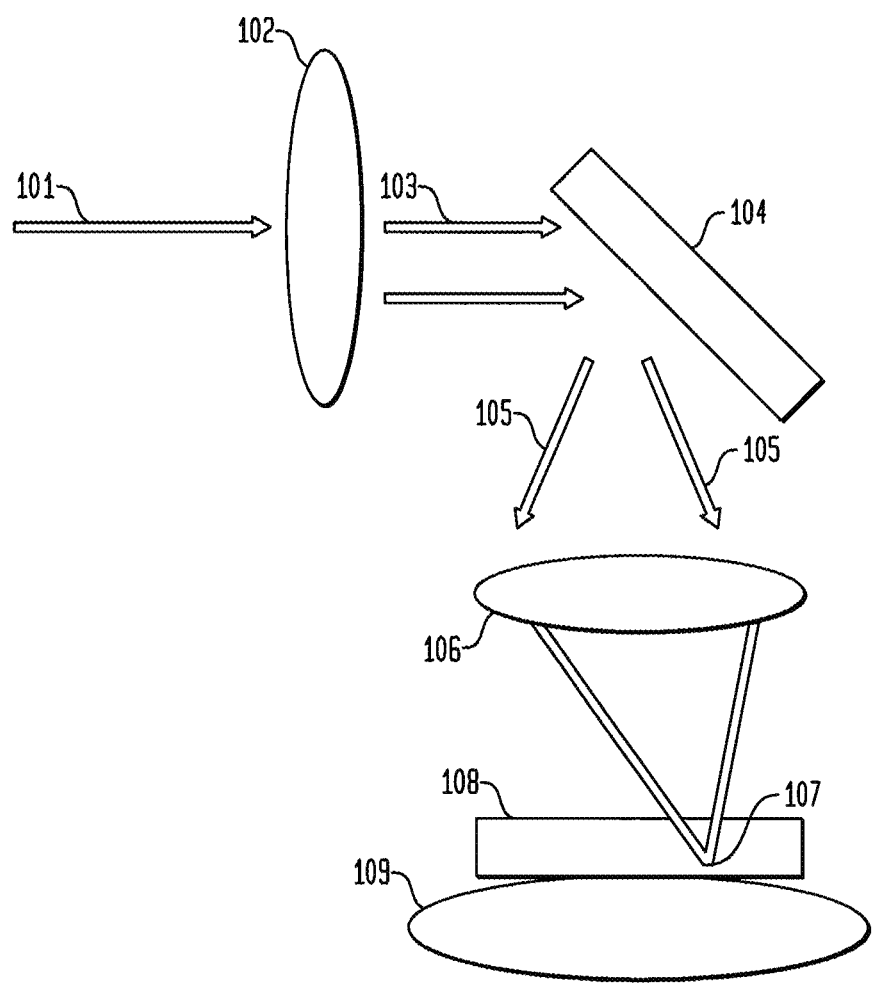
FIG. 2 illustrates a mirror based optical scanning apparatus, according to an embodiment of the present invention.
Figure 4A:
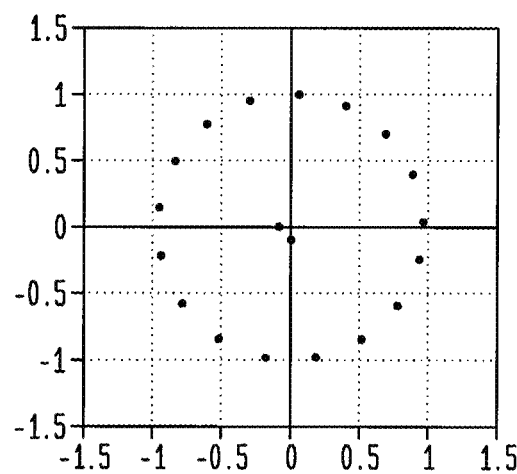
FIGS. 4A-4C illustrate the relationship between the angular velocity of one or more wedge prisms and the depth scan rate of a sensor in relation to the scan pattern of the sensor, according to an embodiment of the present invention.
Figure 4B:
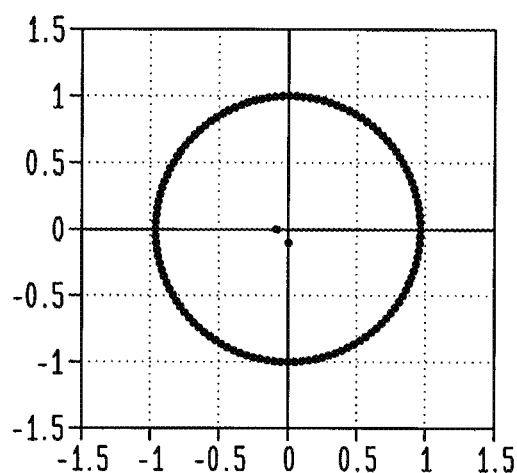
Figure 4C:
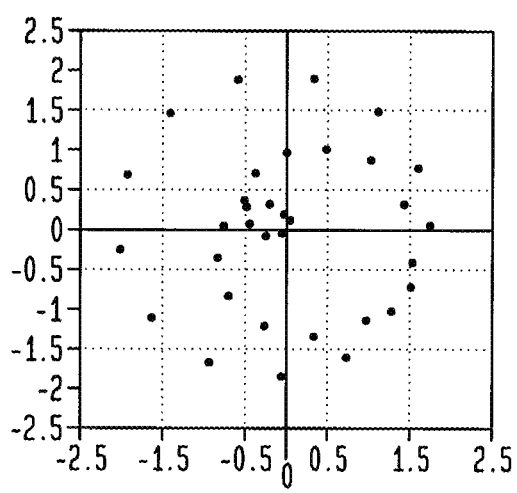
Figure 5A:
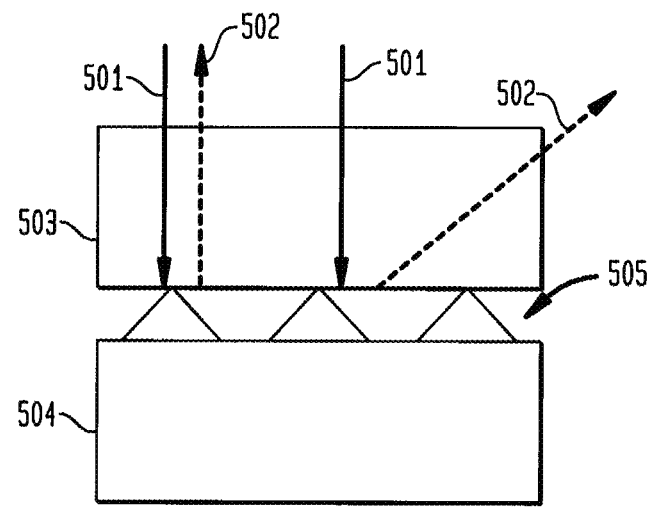
FIG. 5A presents a magnified view of the optical interface between an optical window and a surface of skin.
Figure 5B:
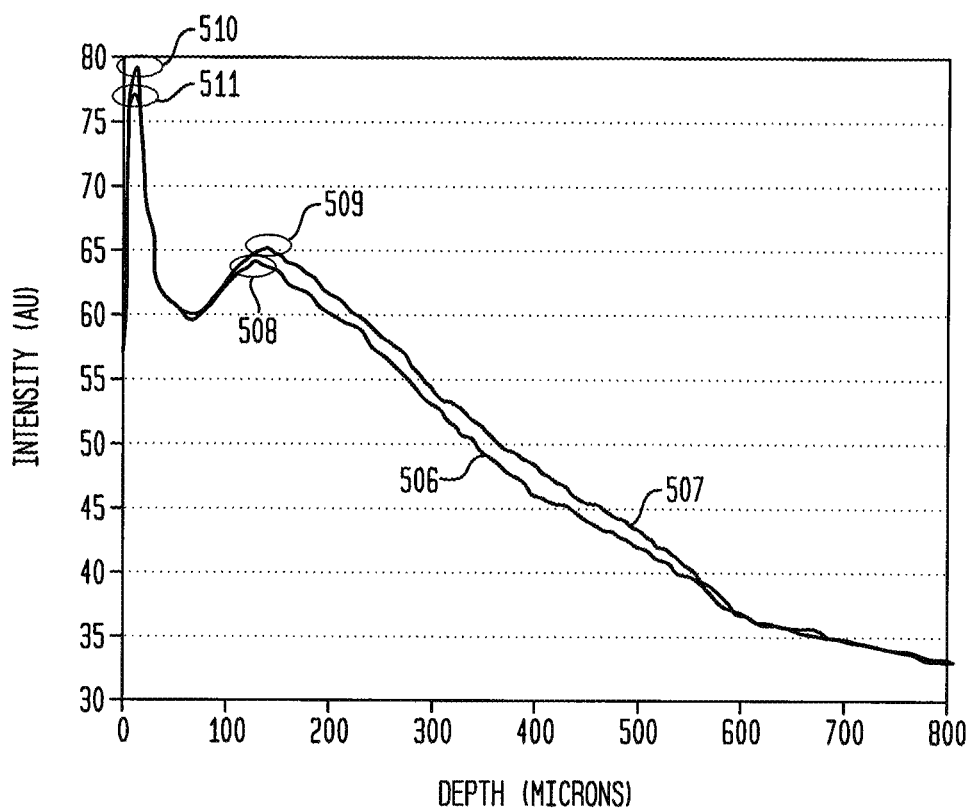
FIG. 5B illustrates the effect of sweat and bodily fluids on the data produced by an optical signal.
Figure 5C:
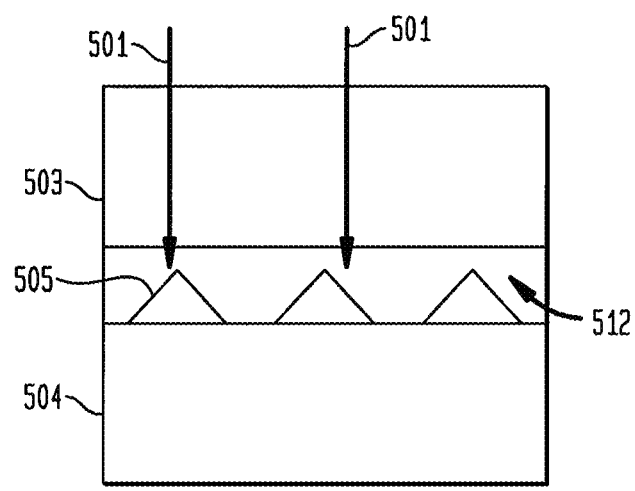
FIG. 5C presents a magnified view of the effect of sweat and bodily fluids on an optical interface between an optical window and a surface of skin.
Figure 6A:
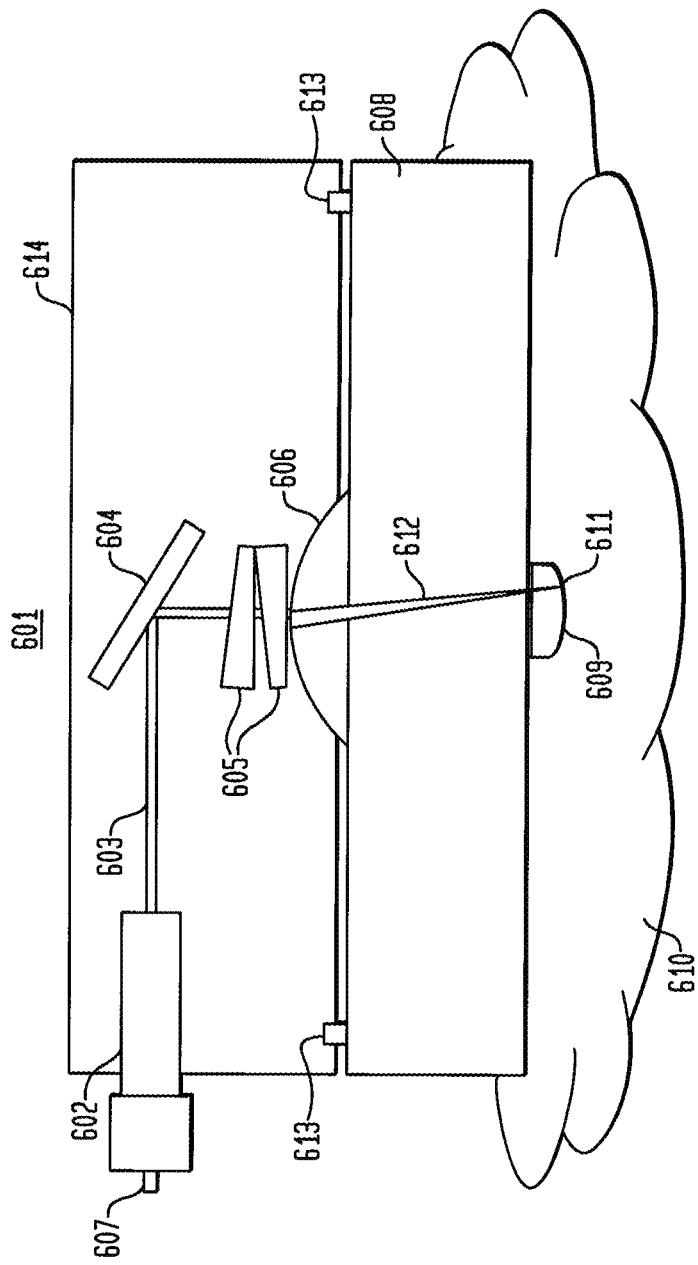
FIG. 6A presents an optical sensor system, according to an embodiment of the present invention.

FIG. 6A presents an optical scanning apparatus system or sensor system for taking blood glucose measurements, according to an embodiment of the present invention. Specifically, the sensor system in FIG. 6A includes a dual wedge prism sensor housing 614 attached to a disposable optical lens apparatus 608 with a Petzval surface 609. In FIG. 6A, sensor system 601 comprises a sensor housing 614 that includes a collimator 602 connected to a light source at a connecter 607, wherein the light source produces a collimated light 603. An example of a connecter is a fiber-optic cable. The collimated light 603 hits a fixed mirror 604, which bends the collimated light 603 to a ninety degree angle. The collimated light 603 passes through rotating dual wedge prisms 605 that deviate the angle of collimated light 603 off the optical axis of the sensor 601. The amount of deviation is based on the thickness of each wedge prism 605 that the collimated light 603 passes through as the wedge prisms 605 rotate. The collimated light 603 then passes through a focusing lens 606, which combines the collimated light 603 into converged light 612, and facilitates focusing the converged light 612 to the focal plane and focal point 611. The converged light 612 then passes through a disposable optical apparatus 608. The disposable apparatus 608 provides an interface between the sensor and the surface of the skin 610 and facilitates setting a distance from focusing lens 606 to the focal plane that is fixed at the skin surface 610 by positioning the interface of the skin surface 610 with the optical window 608 to the focal plane. Because the focal point 611 traces out a curved path as it deviates from the optical axis, attached to the bottom surface of the disposable apparatus 608 is a Petzval dome 609 that acts as an optical window and focuses the focal point 611 onto the surface of the skin 610. As shown in FIG. 6A, the Petzval surface 609 is a separate component physically attached to the bottom surface of the disposable apparatus 608. Alternately, the Petzval surface 609 may be integrally formed from the same material as the disposable apparatus 608. A data collecting device, such as a computer may connect to the sensor housing 614 via the connector 607.

Figure 6B:
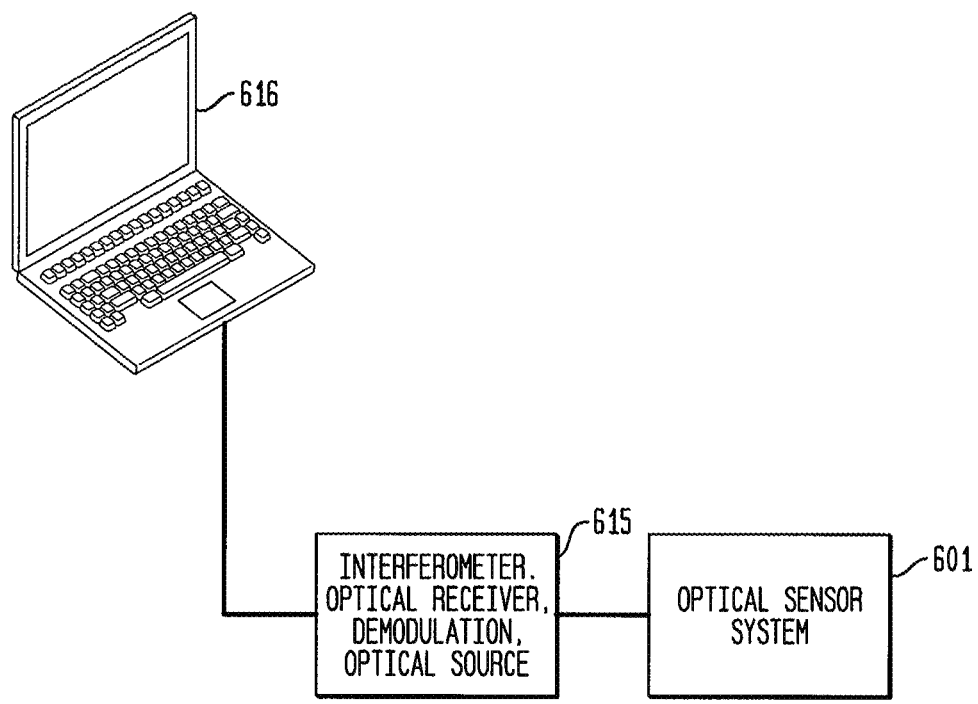
FIG. 6B presents an optical scanning system, according to an embodiment of the present invention.

In FIG. 6B, an interferometer, an optical receiver, a demodulator, and an optical source may be miniaturized and coupled directly to the sensor housing via the connector 607, as shown at 615, making the sensor a "sample arm" of the interferometer. Additionally, the interferometer 615 may be connected to a computer 616 that downloads the sensor data and manipulates the data to produce a blood level glucose or other physiological reading.

In FIG. 6A, the disposable optical lens apparatus 608, including the focusing lens 606 and the Petzval surface 609, may be attached and left on the skin 610 using a topical adhesive, such as, for example, cyanoacrylate or medical adhesive, such as 3M Medical Adhesive. The sensor housing 614 then attaches to the disposable apparatus 608 at connectors 613. When a patient has completed taking a glucose reading, the patient may remove the sensor housing 614 and leave the disposable apparatus 608 attached to the skin. Thus, for the next glucose reading, which may be at some later point in time, perhaps after a meal, the patient need not worry about trying to place the sensor system 601 in the same location as the previous reading in order to produce comparable results. Instead, the patient may merely attach the sensor housing 614 to the disposable apparatus 608 using connectors 613 whenever a glucose reading is desired. The disposable apparatus 608 then may be removed and discarded at the end of a day, for example, and replaced with a new disposable apparatus 608 the following day. Alternately, the patient may leave the sensor housing 614 attached to the disposable apparatus 608 for an extended period of time to permit continuous blood glucose readings.

Figure 7A:
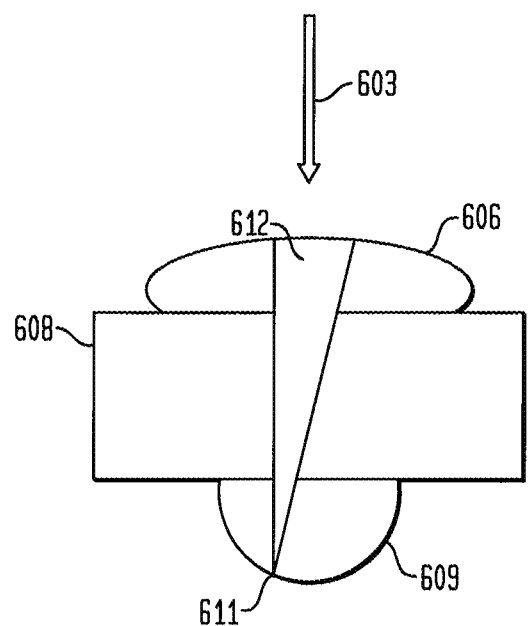
FIG. 7A presents a Petzval surface design for a disposable optical lens apparatus, according to an embodiment of the present invention.
Figure 7B:
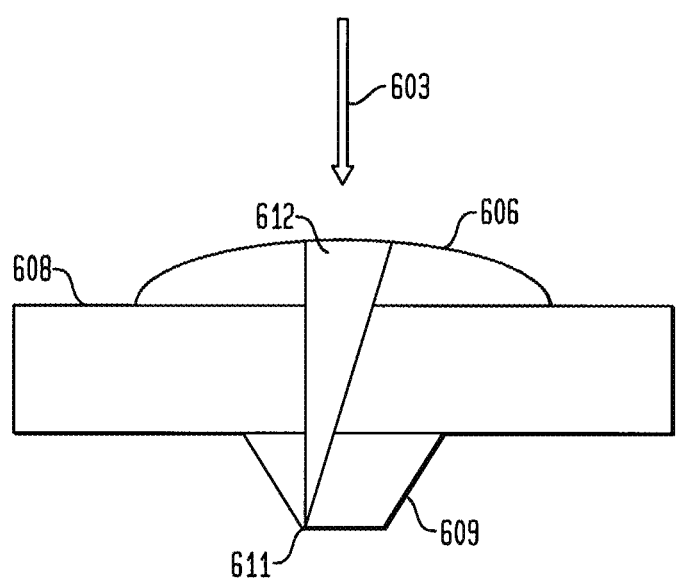
FIG. 7B presents a pedestal surface design for a disposable optical lens apparatus, according to an embodiment of the present invention.

FIGS. 7A and 7B present disposable optical lens apparatuses, according to an embodiment of the present invention. As shown in FIG. 7A, collimated light 603 pass through the focusing lens 606 and combine to become converged light 612 to pass through the disposable optical apparatus 608. The converged light 612 focus into focal point 611 on the focal plane. The focal plane is captured by the dome-shaped Petzval surface 609 attached to the bottom surface of the disposable apparatus 608. The Petzval surface 609 ensures that the focal point 611 remains at the skin interface to optimize the amount of light entering and exiting the skin 610. FIG. 7B presents a similar design of a disposable optical apparatus 608, but with a pedestal-shaped optical window 609, according to an embodiment of the present invention.

Figure 8:
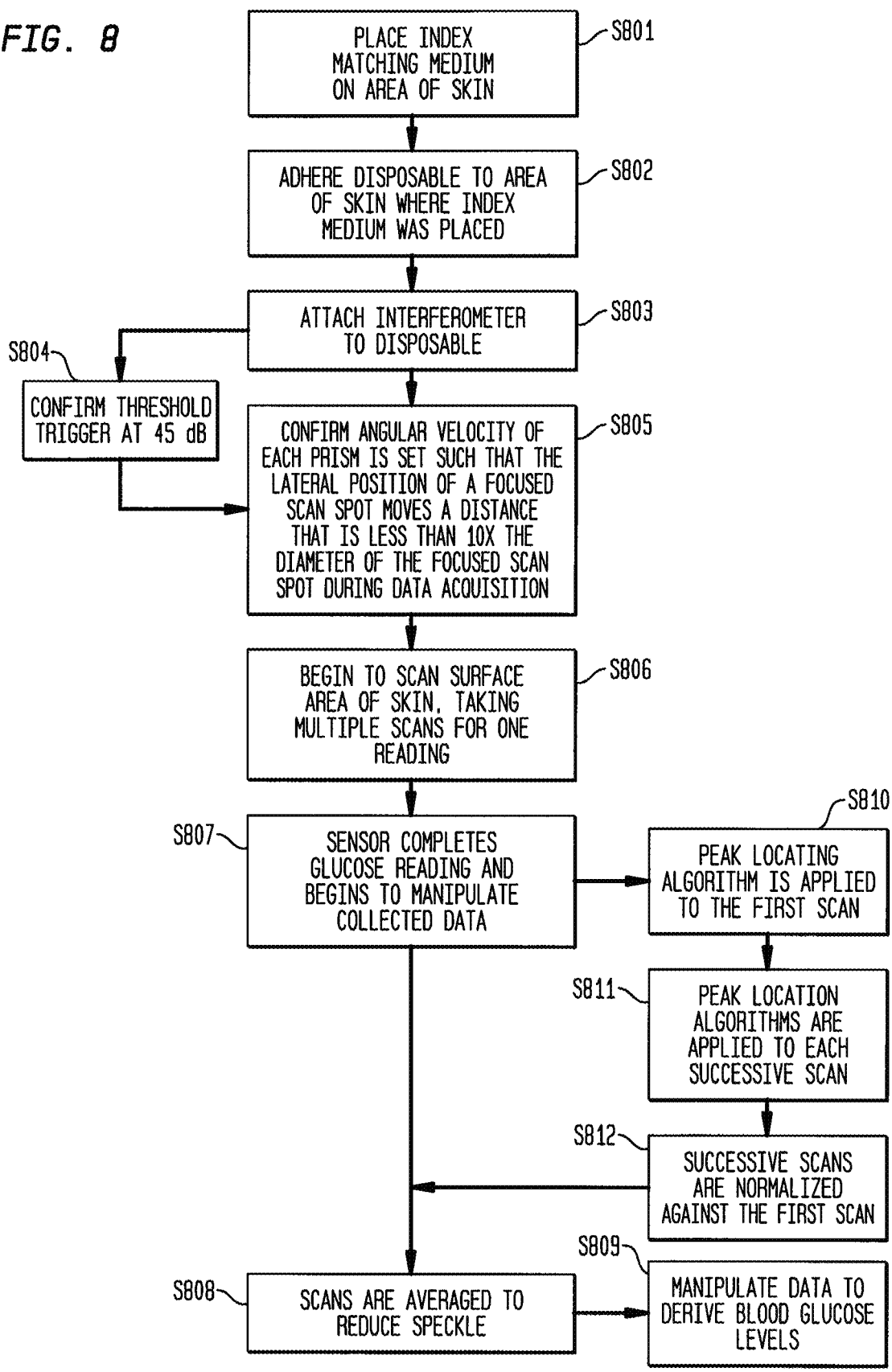
FIG. 8 presents a method of using an optical scanning apparatus to measure blood glucose, according to an embodiment of the present invention.

FIG. 8 presents an exemplary method of using the optical sensor system 601 for blood glucose measurements. The steps of the method need not be in the sequence illustrated, and some steps may occur essentially simultaneously. At step S801, a patient may place or rub an index matching medium, such as glycerine, onto an area of skin 610 where a blood glucose reading is to be taken. Use of an index matching medium facilitates matching the indices of refraction between the material of the Petzval surface 609 with the patient's skin 610 in order to optimize the amount of light that enters and exits the skin 610, and expedites the time required for the Petzval surface 609 to reach equilibrium with the skin surface 610. For example, if the material used in the Petzval surface 609 has an index of refraction of 1.5 and the patient's skin 610 has an index of refraction of 1.3, then without an index matching medium some of the focused converged light 612 entering the skin is lost due to the lower index of refraction of the skin 610. Accordingly, not all of the light exits the skin 610 due to the lower index of refraction, which causes a loss of data. By using an index matching medium with, in this example, a refractive index of 1.4, the medium provides an optical transition for the converged light 612 between the Petzval surface 609 and the skin 610, which increases the amount of light that enters and exits the skin 610. Without the index matching medium, a patient would have to wait upwards of 60 to 90 minutes for the skin to produce sweat and other skin oils at the area where the disposable is placed, in order to optimize the data collection of the sensor.

With the medium in place, at step S802, the patient may adhere the disposable lens apparatus 608 to the area where the index matching medium was placed. Common adhesives such as cyanoacrylate or medical adhesive may be used to secure the disposable apparatus 608 to the skin 610. Once the patient feels that the disposable apparatus 608 is secure, at step S803, the patient couples the sensor housing 614 to the disposable apparatus 608 using the connectors 613.

At step S804, sensor diagnostics verify that a threshold trigger of 45 dB has been pre-set to normalize the scans and resolve for variations in the optical path lengths of the scans produced by the rotating wedge prisms 605 and, accordingly, the change in the thickness of each wedge prism 605 during the rotations. At step S805, sensor diagnostics verify that the angular velocity of each wedge prism 605 has been pre-set to a value such that the lateral position of each focused scan spot moves less than 10× the diameter of the focused scan spot during the data acquisition of the depth scan. For example, if focused scan spot size has a diameter of 20 microns, then the angular velocity is set to a value such that the focused beam 611 does not move laterally more than 200 microns during the depth scan. By setting the angular velocity of each wedge prism 605 to such a value, the distortion in the depth scale of each scan produced by the change in thickness of the wedge prism 605 as it rotates is minimized. The threshold trigger, depth scan rate and angular velocities are presets that may be optimized and built into the sensor system 601.

At step S806, the patient sets the sensor system 601 to begin scanning the skin 610. Since a threshold trigger was set at 45 dB in step S804, the sensor system 601 will not accumulate scan data until the intensity of the optical signal produced by the sensor system 601 reaches a value of 45 dB. Preferably, the threshold is above the highest noise peak produced by the signal but at least 10 dB lower than the intensity peak at the interface between the skin 610 and the disposable apparatus 614.

Once the sensor system 601 has completed taking multiple scans, preferably around 1500 scans, at step S807, the sensor housing 614 may be removed from the disposable apparatus 608, or, alternately, the sensor housing 614 may remain and begin to take another glucose reading. The disposable apparatus 608 remains adhered to the patient's skin 610. The scan data then is manipulated by computer 616 connected to the interferometer 615. Because the threshold trigger was used, all the scans taken begin at a signal intensity of 45 dB, which is equivalent to Time 0, and accordingly, at step S808, the scans are averaged to reduce the speckle associated with the sensor 601. At step S809, the averaged scan data is manipulated using algorithms, such as those described in U.S. Provisional Applications Nos. 60/671,007 and 60/671,285, to derive blood glucose levels. At any later time, such as after a meal, the patient may reattach the sensor housing 614 to the disposable apparatus 608 to take another glucose measurement.

Alternately, the sensor system 601 may be designed to not use a threshold trigger setting at S804, and may normalize the scans once the data has been acquired. For example, once the sensor completes a glucose reading at step S807, computer 616 of the sensor system 601 may apply a peak locating algorithm such as, for example, Gaussian peak fitting, to the first scan to locate the first peak, at step S810. Once step S810 has been completed, the peak locating algorithm is applied to each successive scan, as shown at step S811. At step S812, the successive scans are normalized in depth against the first scan by essentially designating the location of each peak as at Time 0, in order to average the scans together. Thus, any distortion in the optical path length due to the change in the thickness of the wedge prisms 605 as they rotate is removed.

Figure 9:
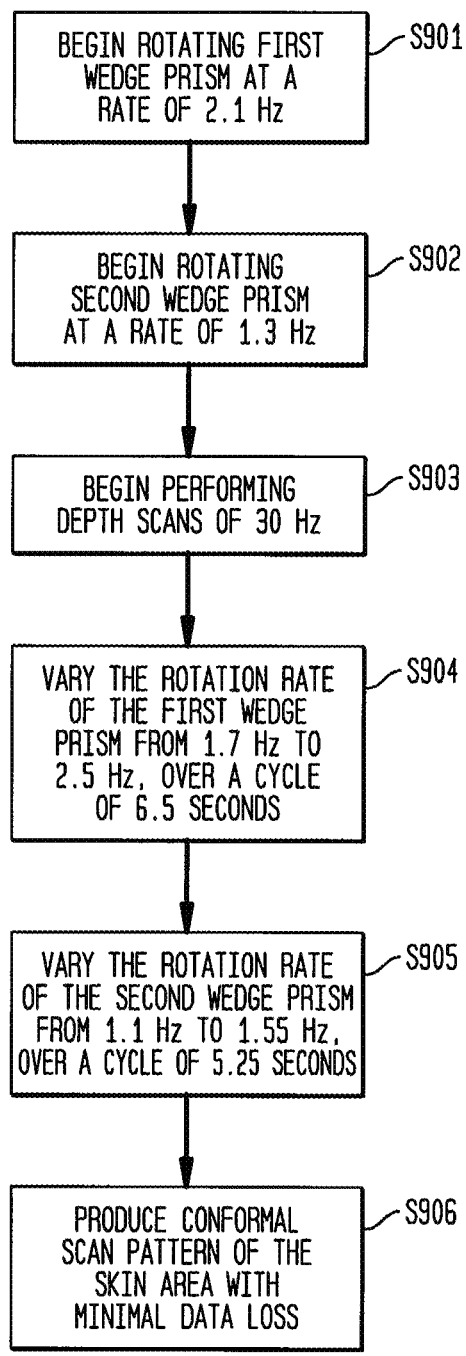
FIG. 9 presents a method for stabilizing a scan pattern of an optical scanning apparatus, according to an embodiment of the present invention.

FIG. 9 presents an exemplary method for stabilizing the scan pattern of sensor 601 and is discussed in conjunction with FIG. 10A, which is a graphical illustration of varying the angular velocities of the dual wedge prisms 605 of sensor system 601. When using the sensor system 601 to take a blood glucose measurement, the first wedge prism 605 begins rotating at a rate of 2.1 revolutions per second ("rps"), which is equivalent to 2.1 Hz, at step S901, as shown at 1001 in FIG. 10A. Similarly, at step S902, the second wedge prism 605 begins rotating at a rate of 1.3 Hz, as shown at 1002, where 2.1 Hz and 1.3 Hz are not integrals of each other. The sensor system 601 then begins to perform depth scans at a rate of 30 Hz, at step S903. An integral of 30 Hz is 2 Hz (i.e., 2 multiplied by 15 equals 30). Additionally, another integral of 30 Hz is 1.5 Hz (i.e., 1.5 multiplied by 20 equals 30 Hz). Thus, although the wedge prisms 605 begin to rotate at rates that are non-integrals of 30 Hz, if the angular velocities 1001, 1002 of both wedge prisms 605 remain at 2.1 Hz and 1.3 Hz, the angular velocities may drift towards 2.0 Hz and 1.5 Hz, thereby becoming integrals of 30 Hz, and preventing conformal coverage of the scan pattern area of the skin 610.

To prevent the angular velocities from becoming integrals of the depth scan rate and remaining at the integral rates, both angular velocities 1001 and 1002 of the wedge prisms 605 are varied over time, in relation to the depth scan rate and in relation to each wedge prism 605, as shown in FIG. 10A. At step S904, the angular velocity 1001 of the first wedge prism 605 is varied as the sensor system 601 continues to perform depth scans. In FIG. 10A, the angular velocity 1001 of the first wedge prism 605 is sinusoidal, oscillating from 2.5 Hz to 1.7 Hz, over a period of 6500 milliseconds, or 6.5 seconds. At step S905, the angular velocity 1002 of the second wedge prism 605 is varied independent of the angular velocity 1001 of the first wedge prism 605, as shown in FIG. 10A. In FIG. 10A, the angular velocity 1002 of the second wedge prism 605 is sinusoidal, oscillating from 1.55 Hz to 1.1 Hz, over a period of 5250 milliseconds, or 5.25 seconds. Thus, although the angular velocities of both wedge prisms 605 may hit a harmonic of 30 Hz during the variation, the angular velocities only remain an integral of 30 rpm for one or two depth scans before the velocities change, thereby minimizing the loss of depth scan data due to the angular velocities being integrals of the depth scan rate. The result is a random, conformal mapping of the scanned surface area of the skin 610 with minimal overlapping within the results, as shown at step S906.

Figure 10B:
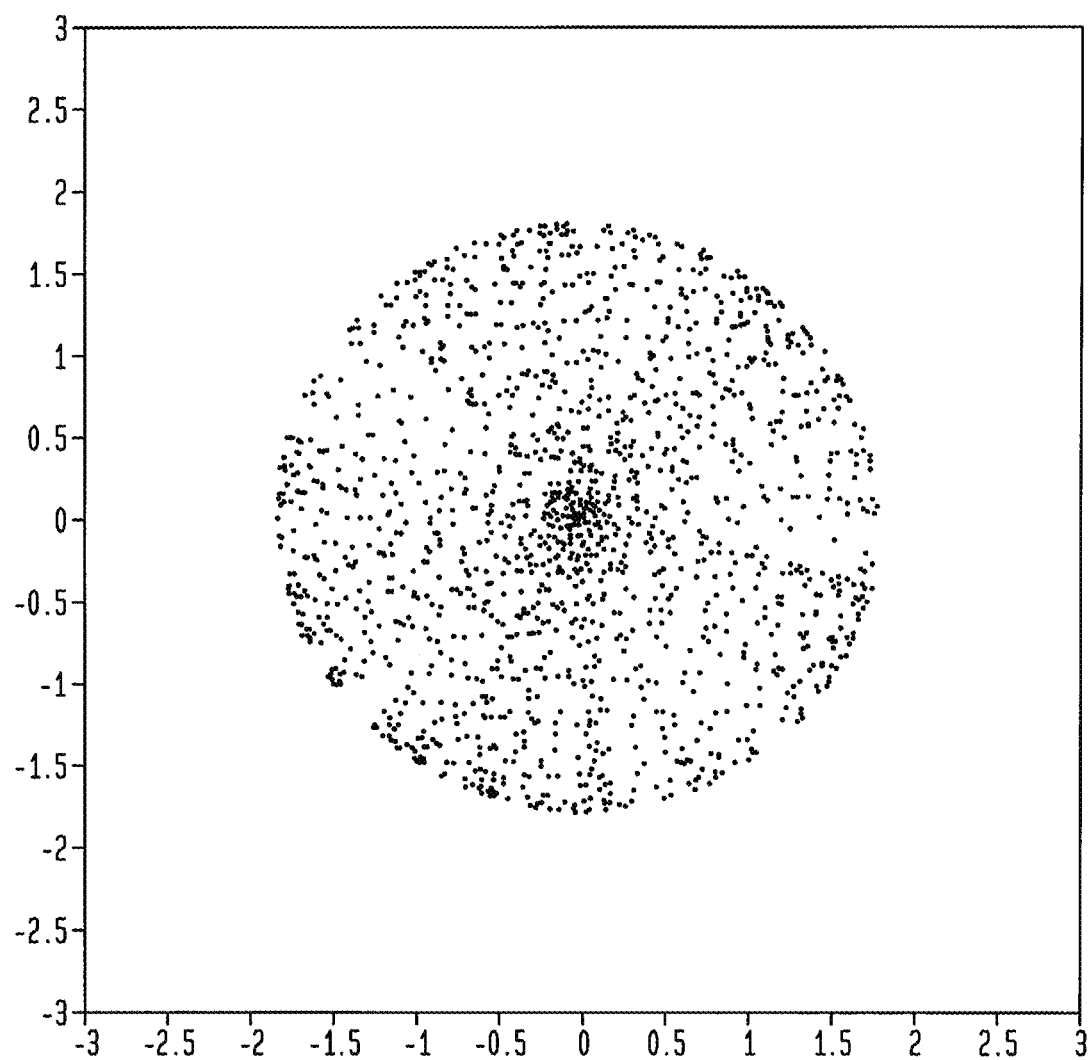
FIG. 10B illustrates the effect of varying the angular velocities of dual wedge prisms in an optical scanning apparatus in comparison to the depth scan rate of the sensor apparatus, according to an embodiment of the present invention.

FIG. 10B illustrates the results of varying the angular velocities of the wedge prisms 605 over time with respect the depth scan rate of sensor system 601 and with respect to each wedge prism 605. By minimizing the potential for a harmonic phase to be created between the depth scan rate and the angular velocities of the wedge prisms 605, conformal coverage of the area of skin 610 scanned is optimized, with each dot representing a position of an individual depth scan on the skin 610.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A system configured to resolve variations in an optical path length of an optical sensor system having at least one angled mirror for measuring blood analyte levels in biological tissue, the system comprising:
   a computer readable storage medium having program instructions embodied therewith; and
   one or more processors configured to execute the program instructions to cause the system to:
      receive a scan of the biological tissue from the optical sensor system, wherein:
         the scan comprises a depth scan into the biological tissue,
         the scan further comprises reflection of light on the at least one angled mirror and transmission of the light into the biological tissue, and
         the at least one angled mirror is configured to oscillate along two axes for at least some of the scan creating variations in the optical path length for at least some of the scan;
      determine a threshold trigger of a signal produced by the optical sensor system; and
      set the optical sensor system to begin acquiring data from the signal once the threshold trigger is reached.

2. The system of claim 1, wherein determining the threshold trigger comprises:
   setting the threshold trigger to a signal intensity value of at least 10 decibels below a first peak intensity value associated with the signal, wherein the first peak intensity value corresponds to an optical interface between the optical sensor system and the biological tissue.

3. The system of claim 2, wherein determining the threshold trigger further comprises:
   setting the threshold trigger to a signal intensity value above a highest noise peak associated with the signal.

4. The system of claim 1, wherein determining the threshold trigger comprises:
   setting the threshold trigger to a signal intensity value that relates to a specific structural feature.

5. The system of claim 4, wherein the specific structural feature corresponds to an optical interface between the optical sensor system and the biological tissue.

6. The system of claim 1, wherein the one or more processors are configured to execute the program instructions to further cause the one or more processors to:
   set an oscillation rate of the at least one angled mirror to a value such that the oscillation rate in both axes of movement of the at least one angled mirror is not a harmonic of a depth scan rate associated with the optical sensor system.

7. A system configured to stabilize a scan pattern of an optical sensor system having at least one angled mirror for measuring blood analyte levels in biological tissue, the system comprising:
   a computer readable storage medium having program instructions embodied therewith; and
   one or more processors configured to execute the program instructions to cause the system to:
      receive a scan of the biological tissue from the optical sensor system, wherein:
         the scan comprises a depth scan into the biological tissue,
         the scan further comprises reflection of light on the at least one angled mirror and transmission of the light into the biological tissue, and
         the at least one angled mirror is configured to oscillate along two axes for at least some of the scan creating variations in an optical path length for at least some of the scan; and
      set an oscillation rate of the at least one angled mirror to a value based on a depth scan rate associated with the optical sensor system.

8. The system of claim 7, wherein the value comprises a non-integral value of the depth scan rate associated with the optical sensor system.

9. The system of claim 8, wherein the one or more processors are configured to execute the program instructions to further cause the one or more processors to:
   vary the oscillation rate of the at least one angled mirror while the optical sensor system is in use.

10. The system of claim 8, wherein the one or more processors are configured to execute the program instructions to further cause the one or more processors to:
    vary the oscillation rate of the at least one angled mirror with respect to a second oscillation rate associated with a second angled mirror during a total time of use of the optical sensor system, wherein the oscillation rate is a non-integral value of the second oscillation rate.

11. The system of claim 7, wherein the one or more processors are configured to execute the program instructions to further cause the one or more processors to:
    set a first oscillation rate associated with a first angled mirror to a harmonic integral of a second oscillation rate associated with a second angled mirror, wherein the first oscillation rate is at least one order of magnitude greater than the first oscillation rate; and
    set the first oscillation rate and the second oscillation rate to non-harmonic integrals of the depth scan rate associated with the optical sensor system.

* * * * *